United States Patent [19]

Spargo et al.

[11] Patent Number: 5,690,963
[45] Date of Patent: Nov. 25, 1997

[54] FREEZE DRIED RED BLOOD CELLS

[75] Inventors: Barry J. Spargo, Baltimore; Alan S. Rudolph, Potomac, both of Md.; Byeong S. Chang, Thousand Oaks, Calif.; Thomas R. Groel, II, Manassas, Va.

[73] Assignee: The United States of America as represented by the Secretary of the Navy, Washington, D.C.

[21] Appl. No.: 497,708

[22] Filed: Jun. 30, 1995

[51] Int. Cl.$^6$ .............................. A61K 35/18; A01N 1/02
[52] U.S. Cl. .............................. 424/533; 435/2; 435/374; 514/23
[58] Field of Search .................. 424/93.73, 533; 514/23; 435/240.2, 2, 374

[56] References Cited

U.S. PATENT DOCUMENTS

| | | | |
|---|---|---|---|
| 3,932,943 | 1/1976 | Briggs et al. | 34/5 |
| 4,287,087 | 9/1981 | Brinkhous et al. | 252/408 |
| 4,874,690 | 10/1989 | Goodrich, Jr. et al. | 435/2 |
| 5,043,261 | 8/1991 | Goodrich et al. | 435/2 |
| 5,045,446 | 9/1991 | Goodrich, Jr. et al. | 435/2 |
| 5,059,518 | 10/1991 | Kortright et al. | 435/6 |
| 5,153,004 | 10/1992 | Goodrich, Jr. et al. | 424/533 |
| 5,171,661 | 12/1992 | Goodrich, Jr. et al. | 435/2 |
| 5,178,884 | 1/1993 | Goodrich et al. | 424/533 |
| 5,213,814 | 5/1993 | Goodrich, Jr. et al. | 424/532 |
| 5,242,792 | 9/1993 | Rudolph et al. | 435/2 |
| 5,340,592 | 8/1994 | Goodrich et al. | 424/533 |

OTHER PUBLICATIONS

Sowemimo–Coker et al. Refrigerated storage of lyophilized and rehydrated, lyophilized human red cells. *Transfusion* 33:322–329 (1993).

Goodrich et al. Preservation of metabolic activity in lyohilized human erythrocytes. *Proc. Natl. Acad. Sci USA* 89: 967–971 (1992).

*Primary Examiner*—Irene Marx
*Assistant Examiner*—Janet M. Kerr
*Attorney, Agent, or Firm*—Thomas E. McDonnell; Ralph T. Webb

[57] ABSTRACT

A process and medium are disclosed for the lyophilization of cells, specifically red blood cells and platelets, and cell-like matter, which comprises the use of solution including a carbohydrate, and biocompatible polymers to permit reconstitution of transfusably useful cells which are viable by the measure of ATP and 2,3 DPG.

4 Claims, No Drawings

FREEZE DRIED RED BLOOD CELLS

INTRODUCTION

Blood is a major tissue of the human body, and has a predominant role in the delivery of oxygen from the lungs to peripheral tissues. This role is carded out by erythrocytes, i.e., red blood cells (RBC). The oxygen is furnished to the peripheral cells from the lungs by an exchange-diffusion system brought about by a red, iron-containing protein called hemoglobin. When hemoglobin combines with oxygen, oxyhemoglobin is formed and after oxygen is given up to the tissues, the oxyhemoglobin is reduced to deoxyhemoglobin.

The red cell membrane is composed of two major structural units, the membrane bilayer and a cytoskeleton. A lipid bilayer and integral membrane proteins form the membrane bilayer. The other major component, the membrane skeleton, stabilizes the membrane bilayer and provides shape and structural integrity. The cytoskeleton is linked to the bilayer in the erythrocyte membrane by lipid-protein as well as protein-protein associations. The hemoglobin, and other RBC components such as glycolytic enzymes, are contained within the red cell membrane.

In adults, bone marrow is active in the formation of new red blood cells. Once erythrocytes enter the blood, they have an average lifetime of about 120 days. In an average person, about 0.83% of the erythrocytes are destroyed each day by phagocytosis, hemolysis or mechanical damage in the body, and the depleted cells are renewed from the bone marrow.

A wide variety of injuries and medical procedures require transfusion of whole blood or a variety of blood components. Every patient does not require whole blood and, in fact, the presence of all the blood components can cause medical problems. Separate blood fractions can be stored under special conditions best suited to assure their biological activity at the time of transfusion. For example, when donor blood is received at a processing center, erythrocytes are separated and stored by various methods. Red blood cells are storable in citrate-phosphate preservative at 4° C. for up to 42 days, generally as a unit of packed erythrocytes having a volume of from 200 to 300 mls and a hematocrit value (expressed as corpuscular volume percent) of 70–90%. Frozen storage in a glycerol solution at −65° C. or lower permits longer shelf life (up to 10 years) but requires maintenance of low temperatures and the extensive washing of the thawed cells to remove the glycerol.

Lyophilization of RBCs provides an alternative preservation method. Lyophilized cells can be stored at room temperature for an extended period of time and easily reconstituted for use. Further, lyophilization improves both shelf life and transportation logistics. However, in order to fulfill their normal oxygen-carrying functions after reconstitution, it is crucial to maintain normal metabolic, biophysical and biochemical properties of RBCs during preservation. Several specific in vitro variables can be used to assess the quality of the lyophilized RBCs upon reconstitution. Such variables include the levels of cellular nucleotides including ATP, ADP, AMP, 2,3-diphosphoglycerate (2,3 DPG), and lactate. In particular, levels of ATP and 2,3 DPG, two products of glycolysis which act to regulate the oxygen affinity of hemoglobin, are a reliable measure of proper cell function and erythrocyte usefulness at a therapeutic level.

Several methods for the lyophilization of RBCs have been disclosed. Such methods are disclosed in R. Goodrich, U.S. Pat. Nos. 5,171,661, 5,178,884, 5,153,004, 4,874,690 and 5,043,261. When RBCs are lyophilized according to previous methods, the reconstituted cells are damaged to the extent that the reconstituted cells are not capable of carrying adequate amounts of oxygen.

Therefore, there is a dire need for a method for lyophilizing or freeze-drying RBCs/or hemosomes which will provide reconstituted cells which are viable and capable of glycolytic metabolism and producing high levels of cellular ATP and 2,3 DPG, for normal RBC function after transfusion.

SUMMARY

The present invention provides a process and composition for freeze-drying RBCs or platelets which overcomes the deficiencies of previous methods. The process of the present invention allows for significantly reduced residual water content over previously patented processes with a potential for significantly increased shelf life of the freeze-dried product. Further, the present process reduces the need for post-processing for removal of cryoprotectant. Most importantly, the composition of the present invention provides freeze-dried RBCs which, when reconstituted, are viable and are capable of producing high levels of cellular nucleotides.

Briefly, the process of the present invention comprises incubating the RBCs in a special buffer formulated to maintain the cells biologically active, loading the cells with glucose, and lyophilizing the cells in a specific process dependent upon the specially formulated buffer such that lyophilized reconstituted cells are viable and maintain a high level of ATP and 2,3 DPG.

It is one object of the present invention to provide a process for the lyophilization of RBCs.

It is another object of the present invention to provide a composition for the lyophilization of RBCs.

It is yet another object of the present invention to provide a composition of freeze-dried cells which have been freeze-dried according to the process of the present invention which, when reconstituted, have high levels of cellular ATP and 2,3 DPG, and are transfusably useful.

DETAILED DESCRIPTION

While the present invention can be applied to hemosomes in general, it will be described in connection to red blood cells in particular.

The process of the present invention includes pre-incubating the RBCs in a buffer specially formuated to increase the levels of intracellular ATP and 2,3 DPG via de novo synthesis. The buffer of the present invention consists of a phosphate-phosphate-citrate buffer, or more simply a phosphate-citrate buffer. The buffer is composed of glucose, at a concentration range of 10–1500 mM, preferably about 139 mM. Other buffer constituents can include: sodium citrate at a range of 1–50 mM, preferably at a concentration of about 33.3 mM; sodium phosphate, dibasic, at a range of 1–50 mM, preferably at a concentration of about 12.0 mM; sodium phosphate, monobasic, at a range of 1–15 mM, preferably at a concentration of about 2.9 mM; ammonium phosphate, at a range of 1–100 mM, preferably at a concentration of about 40.0 mM; and adenine, at a range of 0–5 mM, preferably at a concentration of about 2.0 mM. The buffer can be prepared in distilled water, approximately 330 mOsmolar or isoosmotic, in a pH range of about 7.2–7.4. The cells are pre-incubated in the above-described buffer for about 1 hour to about 7 days, more preferably for about 12 to about 24 hours, most preferably about 20 hours.

After pre-incubation, the cells are loaded with carbohydrate by incubating RBCs in the phosphate-citrate buffer described above further containing a carbohydrate. The carbohydrate may be a monosaccharide, preferably glucose. Even though other sugars can be substituted for glucose including, maltose, trehalose and sucrose (disaccharides), glucose is preferred since it is thought to be easily transported or capable of diffusing across the membrane of the RBC and providing protection to the proteins in the system, namely the hemoglobin, and to some degree the internal lipid membrane. This incubation step is critical although the length of incubation is not. For example, incubation overnight at 4° C., or incubation for 1 hour at 25° C. has a similar effect; adequate time should be given for sufficient glucose to be transported or to diffuse across the membrane where it can protect the hemoglobin. In the absence of this step, the met-hemoglobin (oxidized hemoglobin which cannot carry oxygen) levels are very high and detrimental to RBC function. The concentration of glucose in the loading buffer can be in the range of about 0.1 to 1.5M, preferably in the range of about 0.5 to 1.0M, most preferably in the range of about 0.75 to 1.0M.

Following incubation in the carbohydrate as described above, the erythrocytes are resuspended in lyophilization buffer consisting of the phosphate-citrate buffer described above with the addition of a polymer. The polymer may be present in the solution in concentrations of from between 10–30% (w/v). Preferably the polymer has a molecular weight in the range of 100–500 kDa, most preferably from about 100 to about 200 kDa, and is present in a concentration of about 10 to about 30%. Any polymer can be used which has the capability of forming a matrix that can support the RBCs during lyophilization, and whereby the collapse of the matrix can be controlled. For example, polymers can be selected from the group consisting of polyvinylpyrrolidone (PVP) and polyvinylpyrrolidone derivatives, dextran and dextran derivatives, and amino acid based polymer (i.e. proteins), and hydroxyethyl starch (HES). Most preferred is the polymer HES in the molecular weight range of 100–400 kDa and an average weight of about 150 kDa. A concentration of 20–30% (w/v) is preferred. HES provides a significant advantage in that it is readily transfusable whereas there is a requirement to reduce the concentration of PVP to 1 or 2 parts per billion before transfusion.

The term lyophilization is broadly defined as freezing a substance and then reducing the concentration of one of the solutes, namely water, by sublimation and desorption, to levels which will likely no longer support biological or chemical reactions. Usually, the drying step is accomplished in a high vacuum. However, with respect to the storage of cells and particularly erythrocytes, the extent of drying is of critical importance in the ability of cells to withstand long-term storage at room temperature. In the method of the invention, cells may be lyophilized to a residual water content of less than 10 weight %, preferably less than 3%, and still be reconstituted to transfusable, therapeutically useful cells. Cells with about 3% by weight water content made in accordance with the present invention can be stored for up to about 5 years at room temperature, and at 4° C. for longer than about 10 years, and at −20° C. for even longer than 10 years, for e.g. about 25 years, without decomposition. This far exceeds the current American Association of Blood Bank standard for frozen or refrigerated cells of six weeks at 4° C. or less than one day at room temperature without decomposition.

According to the process of the present invention, lyophilization is accomplished by slow cooling of the erythrocytes suspended in the lyophilization buffer described above. Slow cooling is accomplished for example by placing the cells on the shelf of a temperature controlled shelf lyophilizer and slowly reducing the temperature from room temperature to −15° C. The cells are then incubated at −10° to −15° C. for one hour, or supercooling, a critical step in the proper lyophilization of the RBCs. After supercooling, the temperature is rapidly dropped to −50° C. and held until the vacuum is reduced from 1 ATM to 100 milliTorr (mT) or primary drying. Following primary drying, the shelf temperature is elevated to −15° C. and held for the remainder of the drying phase under a vacuum of 100 mT. When sample temperature reaches shelf temperature of −15° C., the samples are sealed under vacuum and removed from the lyophilizer.

The lyophilization and drying of RBCs described above is critical for the viability of the cells upon reconstitution. Previous lyophilization procedures, such as Goodrich (supra), failed to recognize the importance of the drying process and did not disclose such a process. Upon lyophilization according to the process of the present invention to a moisture content of less than 10%, and preferably less than 3%, the lyophilized cells may be maintained under vacuum in vacuum-tight containers, or under nitrogen or other inert gas, at room temperature for extended periods of time in absence of or without significant degradation of their desirable properties when reconstituted for use as transfusable cells. It is a particular advantage of the present invention that the lyophilized cells may be stored at room temperature for extended periods of time, thus obviating the need for low temperature refrigeration which is required for storing lyophilized red blood cells prepared by methods of the prior art.

It is a further advantage of the present invention that the lyophilized red blood cells may be reconstituted at normal temperatures, i.e. greater than about 17° C. up to about 37° C., which corresponds to normal human body temperature, and preferably at room temperature (about 22° C.). The reconstitution medium is preferably a solution comprising hydroxyethyl starch, present in a concentration of about 20–30%, or a concentration such that a colligative force is present in order to prevent the structural collapse of cells. The reconstitution solution will further be buffered with a buffer solution to maintain a pH within the range of about 7.0 to 7.4. The most preferred reconstitution solution will be a solution similar to the lyophilization solution described above, namely, phosphate-citrate buffer with HES. Other polymers can be used in the reconstitution solution, including PVP and dextran. The lyophilized erythrocytes can be reconstituted by mixing the cells with lyophilization buffer at room temperature and allowing the sample to fully rehydrate. The cells can be used for transfusion when fully hydrated since all of the components present are biocompatible, or phosphate-citrate buffer can be added slowly until the HES concentration is in the range of 0–10% if desirable. Alternatively, the cells can be pelleted and resuspended in 6% hydroxyethyl starch in the phosphate-citrate buffer of the present invention or a phosphate-buffered saline solution.

As noted above, the process of the present invention provides a medium for the lyophilization and reconstitution of intact and biologically-active erythrocytes. While the media of the invention are novel it will be understood that apparatus and related techniques are known by those with ordinary skill in the art for the lyophilization of various materials, and cells in particular, and only the specific temperatures and apparatus are employed herein. From this description, one of ordinary skill in the art will be capable of employing the novel media of the invention in the novel process for the freeze-drying and reconstitution of intact, viable red blood cells.

The present process includes centrifuging whole blood, removing plasma supernatant, and resuspending the pellet in phosphate-citrate buffer of the present invention. This wash cycle can be repeated 2–3 times, then the packed cells are diluted in the phosphate-citrate buffer. Alternatively, commercially available packed blood cells may be used, which typically are prepared in CPDA-1 (commercial solution containing titrate, phosphate, dextrose and adenine) or CPDA-1-like solution, for example, Adsol.

Typically the reconstituted cells of the present invention have a hemoglobin content within 5–10% of the original hemoglobin concentration of that in normal red blood cells. The morphology of the reconstituted cells typically shows no holes or gaps, and discocytic or stomatocytic morphology. The oxygen carrying capacity of normal red blood cells (as measured by P50, the pressure at which 50% of the oxygen molecules are bound) was measured to be in the range of about 25 to 35; with an average Hill coefficient of 1.2–1.9. The typical P50 for erythrocytes lyophilized and reconstituted according to the present invention is about 33 with an average Hill coefficient of 1.8. Assays of ATP in the reconstituted cells indicate ATP levels suggesting normal ATP to ADP metabolism. Assays to 2,3 DPG suggest 150–200% that of fresh RBCs. Normal agglutination of red blood cells according to the present invention is also typically found.

Having described the preferred embodiments of the present invention, the following examples are provided by way of illustration but are not intended to limit the invention in any way.

EXAMPLE 1

Analysis of Present Lyophilization Process and Buffer

A comparison of normal fresh (Table 1: fresh) and CPDA-1 stored RBCs (Table 1: CPDA-1) with RBCs stored in the buffers disclosed herein, namely mARC-8 (Table 1: mARC-8). The mARC-8/HES RBCs (Table 1: mARC-8/HES) were later lyophilized and rehydrated as disclosed. The cells were incubated in their respected buffers for 24 hrs at 4° C. after which measurements were taken for total hemoglobin (Table 1: THb), % oxygenated hemoglobin (% $O_2$ Hb), % $CO_2$, % met-hemoglobin, amount of dissolved oxygen in solution (Vol % O2), oxygen carrying capacity (p50), pH inside the cell (pH internal) and pH in the media (pH external, cell size and cell volume).

Sample Preparation. Human erythrocytes stored in CPDA-1 were used within 72 hours of collection. Erythrocytes were washed twice in 0.9% sodium citrate solution to remove CPDA-1, serum, platelets and lymphocytes using a COBE 2991 (COBE/BCT, Denver, Colo.). Packed erythrocytes were resuspended to a hematocrit of 40% (v/v) in a mARC-8 Buffer containing; 139 mM glucose, 33 mM sodium citrate, 12 mM sodium phosphate-dibasic, 3 mM sodium phosphate-monobasic, 40 mM ammonium phosphate and 2 mM adenine. The erythrocytes, in the mARC-8 solution were stored at 4° C. for 24 hours. The buffer was removed post-incubation following centrifugation and the erythrocytes were resuspended in the mARC-8 Buffer with 0.75M glucose added. The erythrocytes were incubated at 25° C. for 1 hour. Following incubation, the medium was removed by centrifugation and the erythrocytes were resuspended in lyophilization buffer containing; 139 mM glucose, 33 mM sodium citrate, 12 mM sodium phosphate-dibasic, 3 mM sodium phosphate-monobasic, 40 mM ammonium phosphate, 2 mM adenine and 30% (w/v) average molecular weight 150 KDa hydroxyethyl starch (McGaw, Inc. Irvine, Calif.).

Lyophilization. Immediately following the prepratory phase, erythrocytes in the lyophilization buffer were aliquoted 10 mL into 100 mL vials. The aliquoted samples were placed on the shelf of a temperature controlled shelf lyophilizer (FTS Systems, Inc.) The samples were slowly reduced from RT to −15° C. and incubated for 1 hour (supercooling phase). After equilibration at −15° C., the shelf temperature was rapidly dropped to −50° C. and held at that temperature until the vacuum was reduced from 1 ATM to 100 mT (primary drying phase). Following primary drying, the shelf temperature was elevated to −15° C. and held for the remainder of the drying phase under a vacuum of 100 mT. When the sample temperature reached the shelf temperature of −15° C., the samples were sealed under vacuum and removed from the lyophilizer. Residual water content was determined using the Mettler LP-16 (Mettler Instrument Corp., Hightstown, N.J.).

Rehydration. Samples were rehydrated in a two step method using a buffer containing; 139 mM glucose, 33 mM sodium chloride, 12 mM sodium phosphate-dibasic, 3 mM sodium phosphate-monobasic, 40 mM ammonium phosphate, 2 mM adenine and 30% (w/v) hydroxyethyl starch. Once the samples were fully rehydrated, hydroxyethyl starch concentration was reduced to between 6–10% by the slow addition of a buffer containing; 139 mM glucose, 33 mM sodium chloride, 12 mM sodium phosphate-dibasic, 3 mM sodium phosphate-monobasic, 40 mM ammonium phosphate, 2 mM adenine. The erythrocytes were isolated by centrifugation, resuspended and washed twice in mARC-8.

Post-Rehydration. The erythrocytes were analyzed to determine cell integrity and function. The methoxy hemoglobin values were measured via IL-282 Co-oximeter (Instrumentation Laboratories, Lexington, Mass.). Oxygen carrying capacity (P50) was determined using a Hemox-Analyzer (TCS, Inc. Southampton, Pa.). The cell sizing and volume were measured with a Coulter Multisizer II (Coulter Electronics, LTD, Beds, England).

TABLE 1

| SAMPLE | THb | % O2 Hb | % CO | % MET Hb | Vol. % O2 | P50 | pH internal | pH external | Cell Size (um) | Cell Volume (um3) |
|---|---|---|---|---|---|---|---|---|---|---|
| PRE-LYOPHILIZATION | | | | | | | | | | |
| Fresh | 5.8 | 102.1 | −23.5 | 0.5 | 18.7 | 28 | 7.31 | 7.26 | 4.236 | 41.51 |
| CPDA-1 | 6.1 | 89.6 | −14.3 | 0.9 | 17.2 | 18 | 7.29 | 7.04 | 4.863 | 60.21 |
| mARC-8 | 6.3 | 92.5 | −7.2 | 1.2 | 5.7 | 24.4 | 7.31 | 7.25 | 5.284 | 68.21 |
| mARC-8/HES | 5.1 | 89.9 | −5.8 | 1.6 | 6.5 | **** | 7.33 | 7.29 | 4.506 | 54.26 |

TABLE 1-continued

| SAMPLE | THb | % O2 Hb | % CO | % MET Hb | Vol. % O2 | P50 | pH internal | pH external | Cell Size (um) | Cell Volume (um3) |
|---|---|---|---|---|---|---|---|---|---|---|
| POST-LYOPHILIZATION | | | | | | | | | | |
| mARC-8 initial | 4.8 | 89.6 | −19.4 | 28.9 | 4.5 | **** | 6.85 | 6.39 | **** | **** |
| mARC-8 post-wash | 3 | 108.4 | −16.5 | 19.2 | 4.4 | 33.7 | 6.94 | 6.72 | 4.475 | 46.91 |
| mARC-8 24 hour | 3 | 96.8 | −15.7 | 17.4 | 4.2 | 35 | 7.05 | 6.88 | 4.396 | 44.48 |

Red blood cells incubated in mARC-8 and HES/mARC-8 maintain clinical values within acceptable ranges. There is little change in the cell size and cell volume. Met-hemoglobin values return to acceptable ranges following the washing step. $P_{50}$ values are increased in buffers containing mARC-8. This is likely due to elevated levels of ATP and 2,3-DPG and are within acceptable range.

EXAMPLE 2

Comparison of Reconstituted Cells Goodrich vs Spargo

RBCs were incubated in either the Cryopharm lyophilization buffer or the lyophilization buffer of the present invention (hereafter referred to as Spargo), and several RBC variables measured.

Table 2A illustrates that red blood cells retain their clinical values following incubation in either the Goodrich lyophilization buffer or Spargo lyophilization buffer embodied herein.

Table 2B represents values from red blood cell samples prepared in either the Goodrich or the Spargo buffer formulation which were lyophilized according to the Goodrich process disclosed in U.S. Pat. No. 5,043,261. Table 2B demonstrates that met-hemoglobin formation was significant in both buffer formulations upon initial rehydration (I). Following the washing steps (P), a significant decline in the total hemoglobin present in both formulations was observed, while only marginal improvement in the met-hemoglobin concentration was achieved. The total hemoglobin and the met-hemoglobin values were well outside acceptable clinical ranges for transfusion.

Table 2C compares the met-hemoglobin and total hemoglobin values obtained from red blood cell samples prepared in either the Goodrich or Spargo buffer formulations and lyophilized according to the process of Spargo embodied herein. There is a significant difference in the initial met-hemoglobin values obtained from cells processed in the different buffer formulations, where the cells processed in the Spargo buffer had met-hemoglobin values significantly lower than the met-hemoglobin values obtained from cells processed in the Goodrich formulation. Following the washing step, met hemoglobin values decreased in RBCs lyophilized in the Spargo formulation reaching values within a clinically acceptable range with total hemoglobin values within 25% of the initial starting value. The Goodrich formulation resulted in RBCs with significantly high met-hemoglobin and extremely low total hemoglobin values compared to initial values.

TABLE 2

Goodrich lyophilization buffer and process compared to Spargo lyophilization buffer and process.

| SAMPLE | THb | % O2 Hb | % CO Hb | % MET Hb | VOL % O2 | % RESIDUAL WATER | TIME ON LYOPHILIZER |
|---|---|---|---|---|---|---|---|
| Table 2.A Pre-Lophilization. Incubation in different buffers | | | | | | | |
| Fresh RBC | 26.8 | 69.8 | −2.5 | 0.9 | 20.2 | N/A | N/A |
| BSH - PVP (Goodrich) | 5.1 | 92.5 | −7.2 | 2.1 | 5.7 | N/A | N/A |
| MARC-8 - HES (Spargo) | 5.3 | 89.9 | −5.8 | 1.6 | 6.5 | N/A | N/A |
| Table 2.B Post-Lyophilization (Goodrich Process using either Goodrich buffer or Spargo buffer) | | | | | | | |
| Goodrich Rehydrated (I) | 4.9 | 96.4 | −41.7 | 79.3 | 2.2 | 16.20% | 114.25 HR |
| Goodrich Rehydrated (P) | 2.3 | 108.3 | −28.2 | 53.2 | 1 | N/A | N/A |
| Spargo Rehydrated (I) | 3.8 | 112.9 | −71.4 | 68.9 | 1.5 | 1.70% | 114.25 HR |
| Spargo Rehydrated (P) | 1.7 | 120.5 | −38.2 | 77.4 | 0.8 | N/A | N/A |
| Table 2.C. Post-Lyophilization (Spargo Process using either Goodrich buffer or Spargo buffer) | | | | | | | |
| Goodrich Rehydrated (I) | 4.5 | 91.1 | −32.1 | 81.4 | 1.1 | 34.60% | 96.25 HR |
| Goodrich Rehydrated (P) | 0.8 | 127.6 | −30.6 | 92.7 | 0.6 | N/A | N/A |
| Spargo Rehydrated (I) | 4.7 | 98.7 | −12.4 | 37.9 | 2.1 | 11.30% | 26.75 HR |
| Spargo Rehydrated (P) | 3.8 | 117.4 | −21.8 | 26.6 | 1.3 | N/A | N/A |

(I) Inital rehydration value, (p) Post wash/processing value

The best values for RBCs were obtained using the Spargo buffer in the Spargo process. In addition, the time on the lyophilizer using the Spargo process was significantly shorter, 114.25 hours vs 26.75 hours and achieved a residual water content of 11.30% as opposed to 16.2% residual water in the Goodrich samples using the Goodrich process and buffer.

EXAMPLE 3

The effects of buffer formulation on the intracellular level of adenosine triphosphate (ATP) and 2,3-diphosphoglycerate (2,3-DPG) were measured. The composition of each of the buffers is shown below the Table 3. Control: Fresh RBCs; CPDA is the blood bank storage media. The cells were lyophilized and rehydrated according to the process described in Example 1.

TABLE 3

|  | ATP umole/g Hb | ADP umole/g Hb | AMP umole/g Hb | 2,3-DPG umole/g Hb |
|---|---|---|---|---|
| Control | 4.22 | 0.436 | 0.031 | 24.2 |
| rehydrated | 2.7 | 0.64 | 5.93 | 21.1 |
| PBS | 1.16 | 1.34 | 1.63 | 1.62 |
| rehydrated | 0.62 | 1.82 | 26.4 | 0.46 |
| CPDA | 1.27 | 1.42 | 1.91 | 4.35 |
| rehydrated | 2.24 | 1.43 | 12.2 | 2.1 |
| mARC-8 | 9.16 | 0.67 | 0.081 | 79.4 |
| rehydrated | 9.14 | 1.2 | 12.5 | 49.1 |

|  | CPDA-1 | mARC-8 |
|---|---|---|
| Glucose | 177 | 139 |
| Na-citrate |  | 33.3 |
| Na2HPO4 |  | 12 |
| NaH2PO4 | 16 | 2.9 |
| (NH4)2HPO4 |  | 40 |
| Adenine | 2 | 2 |
| Citric acid | 17 |  |
| pH | 5.7 | 7.4 |
| mOsm | 297 | 310 |

As can be seen from Table 3, rehydrated lyophilized red blood cells in MARC-8 buffer maintain the high level of ATP and 2,3-DPG. In fact the 2,3-DPG levels in the RBC's in MARC-8 are more than twice those in the control cells.

What is claimed is:

1. A process for treating erythrocytes for storage comprising in order the steps of
   (a) resuspending erythrocytes in a first phosphate-citrate incubation buffer which comprises glucose in a concentration range of 10–1500 mM, sodium citrate in a concentration range of 1–50 mM, sodium diphosphate dibasic in a concentration range of 1–50 mM, sodium phosphate monobasic in a concentration range of 1–15 mM, ammonium phosphate in a concentration range of 1–100 mM and adenine in a concentration range of 0–5 mM;
   (b) incubating the resuspended erythrocytes in said phosphate-citrate incubation buffer;
   (c) removing said first phosphate-citrate incubation buffer;
   (d) resuspending the incubated erythrocytes in a second phosphate-citrate incubation buffer comprising the phosphate-citrate incubation buffer of step (a) and an additional carbohydrate in a concentration of from about 500 to about 1000 mM;
   (e) incubating the resuspended erythrocytes in the second phosphate-citrate incubation buffer;
   (f) removing the second phosphate-citrate incubation buffer;
   (g) resuspending the incubated erythrocytes in a phosphate-citrate lyophilization buffer comprising the phosphate-citrate incubation buffer of step (d) and a polymer having a molecular weight of from about 100 kD to about 500 kD in a concentration of about 10–30% w/v;
   (h) lyophilizing the resuspended erythrocytes of step (g) by the steps of
      (1) slowly cooling the resuspended erythrocytes to −15° C.;
      (2) incubating said cooled erythrocytes at −10° to −15° C.;
      (3) primary drying the erythrocytes of step (2) by further cooling said erythrocytes of step (2) to −50° C. and placing said primary-dried erythrocytes under a vacuum;
      (4) further drying the primary-dried erythrocytes of step (3) by keeping the primary-dried erythrocytes under vacuum while elevating the temperature of said primary-dried erythrocytes to −15° C., until the residual water content of the lyophilized erythrocytes is less than 10% by weight;
   (i) sealing the lyophilized erythrocytes under vacuum for storage; and
   (j) storing the sealed erythrocytes;
   wherein the step (b) of incubating the erythrocytes in the first phosphate-citrate incubation buffer is carried out for a sufficient time such that when the stored erythrocytes of step (j) are subsequently rehydrated, the rehydrated erythrocytes have an ATP level of at least 100% and a 2,3 DPG level of at least 150–200% that of freshly drawn packed erythrocytes.

2. The process of claim 1 wherein the carbohydrate in the second phosphate-citrate incubation buffer is glucose.

3. A process for treating erythrocytes for storage comprising in order the steps of
   (a) resuspending erythrocytes in a first phosphate-citrate incubation buffer which comprises glucose in a concentration range of 10–1500 mM, sodium citrate in a concentration range of 1–50 mM, sodium diphosphate dibasic in a concentration range of 1–50 mM, sodium phosphate monobasic in a concentration range of 1–15 mM, ammonium phosphate in a concentration range of 1–100 mM and adenine in a concentration range of 0–5 mM;
   (b) incubating the resuspended erythrocytes in said phosphate-citrate incubation buffer;
   (c) removing said first phosphate-citrate incubation buffer;
   (d) resuspending the incubated erythrocytes in a second phosphate-citrate incubation buffer comprising the phosphate-citrate incubation buffer of step (a) and an additional carbohydrate in a concentration of from about 500 to about 1000 mM;
   (e) incubating the resuspended erythrocytes in the second phosphate-citrate incubation buffer;
   (f) removing the second phosphate-citrate incubation buffer;
   (g) resuspending the incubated erythrocytes in a phosphate-citrate lyophilization buffer comprising the phosphate-citrate incubation buffer of step (d) and a polymer having a molecular weight of from about 100 kD to about 500 kD in a concentration of about 10–30% w/v;
   (h) lyophilizing the resuspended erythrocytes of step (g) by the steps of
      (1) slowly cooling the resuspended erythrocytes to −15° C.;
      (2) incubating said cooled erythrocytes at −10° to −15° C.;
      (3) primary drying the erythrocytes of step (2) by further cooling said erythrocytes of step (2) to −50° C. and placing said primary-dried erythrocytes under a vacuum;

(4) further drying the primary-dried erythrocytes of step (3) by keeping the primary-dried erythrocytes under vacuum while elevating the temperature of said primary-dried erythrocytes to −15° C., until the residual water content of the lyophilized erythrocytes is less than 10% by weight;

(i) sealing the lyophilized erythrocytes under vacuum for storage; and (j) storing the sealed erythrocytes;

(k) rehydrating the stored erythrocytes of step (j) by suspending said erythrocytes in a phosphate-citrate reconstitution buffer comprising a polymer having a molecular weight of from about 100 kD to about 500 kD in a concentration of about 10–30% w/v at a temperature in the range of 15°–50° C.;

wherein the step (b) of incubating the erythrocytes in the first phosphate-citrate incubation buffer is carried out for a sufficient time such that the rehydrated erythrocytes of step (k) have an ATP level of at least 100% and a 2,3 DPG level of at least 150–200% that of freshly drawn packed erythrocytes.

4. The process of claim 3 including the further step of diluting said phosphate-citrate reconstitution buffer after rehydrating said stored erythrocytes of step (k) in said phosphate-citrate reconstitution buffer so that the concentration of the polymer in said phosphate-citrate reconstitution buffer is in the range of about 6–10% w/v.

* * * * *